United States Patent
Tal et al.

(10) Patent No.: US 11,951,265 B2
(45) Date of Patent: Apr. 9, 2024

(54) VASCULAR ACCESS WIRE TIP COMPRISING A CRANK

(71) Applicant: Embrace Medical Ltd, Tel Aviv (IL)

(72) Inventors: Michael Gabriel Tal, Tel Aviv (IL); Omer Eilon, Nachshonim (IL); Ronny Winshtein, Ramat HaSharon (IL)

(73) Assignee: Embrace Medical Ltd (IL)

( * ) Notice: Subject to any disclaimer, the term of this patent is extended or adjusted under 35 U.S.C. 154(b) by 0 days.

(21) Appl. No.: 18/494,194

(22) Filed: Oct. 25, 2023

(65) Prior Publication Data

US 2024/0050705 A1 Feb. 15, 2024

Related U.S. Application Data

(63) Continuation of application No. PCT/IB2022/057381, filed on Aug. 8, 2022.

(51) Int. Cl.
*A61M 25/06* (2006.01)
*A61M 25/09* (2006.01)

(52) U.S. Cl.
CPC ............. *A61M 25/0606* (2013.01); *A61M 2025/09083* (2013.01); *A61M 2025/09108* (2013.01); *A61M 2207/10* (2013.01); *A61M 2210/12* (2013.01)

(58) Field of Classification Search
CPC .... A61M 25/0606; A61M 2025/09083; A61M 2025/09108; A61M 2207/10; A61M 2210/12
USPC ..................................................... 604/164.13
See application file for complete search history.

(56) References Cited

U.S. PATENT DOCUMENTS

| | | | |
|---|---|---|---|
| 1,879,249 A | 9/1932 | Coy | |
| 2,717,599 A | 9/1955 | Jennie | |
| 2,746,454 A | 5/1956 | Sorensen | |
| 3,521,620 A | 7/1970 | Cook | |
| 4,456,017 A * | 6/1984 | Miles | A61M 25/09033 604/95.04 |
| 4,661,300 A | 4/1987 | Daugherty | |
| 4,716,757 A | 1/1988 | McGregor et al. | |
| 4,904,433 A | 2/1990 | Williamitis | |
| 4,919,605 A | 4/1990 | Kousai et al. | |
| 5,057,083 A | 10/1991 | Gellman | |
| 5,102,324 A | 4/1992 | Bullard et al. | |
| 5,111,829 A | 5/1992 | Toledo | |
| 5,341,818 A | 8/1994 | Abrams et al. | |
| 5,352,205 A | 10/1994 | Dales et al. | |

(Continued)

FOREIGN PATENT DOCUMENTS

| | | |
|---|---|---|
| JP | 2005169012 A | 6/2005 |
| JP | 2006055674 A | 3/2006 |

(Continued)

*Primary Examiner* — Phillip A Gray
(74) *Attorney, Agent, or Firm* — Veros Legal Solutions, LLP (57) ABSTRACT

A vascular access wire is disclosed. The vascular access wire includes an elongated core member and a distal tip. The Distal tip comprising a crank configured with a crank distal surface and a crank center of rotation. The crank is configured to rotate about the crank center of rotation when the core member is sufficiently loaded axially and when the crank distal surface is pressed against a wall of a target blood vessel, for triggering or affecting a deflecting and/or a deforming of the core member proximally to the crank.

41 Claims, 7 Drawing Sheets

(56) References Cited

U.S. PATENT DOCUMENTS

| | | |
|---|---|---|
| 5,365,942 A | 11/1994 | Shank |
| 5,478,328 A | 12/1995 | Silverman et al. |
| 5,484,565 A | 1/1996 | Larsen et al. |
| 5,497,786 A | 3/1996 | Urick |
| 5,531,701 A | 7/1996 | Luther |
| 5,716,572 A | 2/1998 | Lesiczka et al. |
| 5,843,356 A | 12/1998 | Patel et al. |
| 5,857,464 A | 1/1999 | Desai |
| 5,957,865 A | 9/1999 | Backman et al. |
| 5,985,195 A | 11/1999 | Muskatello |
| RE36,628 E | 3/2000 | Sagae et al. |
| 6,596,011 B2 | 7/2003 | Johnson et al. |
| 6,638,266 B2 | 10/2003 | Wilson et al. |
| 6,740,277 B2 | 5/2004 | Howell et al. |
| 6,979,318 B1 | 12/2005 | McDonald et al. |
| 7,029,467 B2 | 4/2006 | Currier et al. |
| 7,762,962 B2 | 7/2010 | Mishima |
| 7,959,595 B2 | 6/2011 | Melsheimer et al. |
| 8,092,395 B2 | 1/2012 | Lupton et al. |
| 8,142,416 B2 | 3/2012 | Stauber |
| 8,936,581 B2 | 1/2015 | Bihlmaier |
| 8,986,225 B2 | 3/2015 | Folk |
| 9,078,994 B2 | 7/2015 | Rosenman et al. |
| 9,757,536 B2 | 9/2017 | Abt et al. |
| 9,987,423 B2 | 6/2018 | Kuracina et al. |
| 9,987,468 B2 | 6/2018 | Bagwell et al. |
| 10,384,039 B2 | 8/2019 | Ribelin et al. |
| 10,441,746 B2 | 10/2019 | Besselink |
| 10,478,592 B2 | 11/2019 | Shevgoor |
| 10,610,668 B2 | 4/2020 | Burkholz et al. |
| 10,820,923 B2 | 11/2020 | Govari |
| 10,987,489 B2 * | 4/2021 | von Segesser .. A61M 25/09041 |
| 2003/0163064 A1 | 8/2003 | Vrba et al. |
| 2004/0167437 A1 | 8/2004 | Sharrow et al. |
| 2005/0049690 A1 | 3/2005 | Boismier et al. |
| 2008/0281156 A1 | 11/2008 | Makower et al. |
| 2009/0076435 A1 | 3/2009 | Melsheimer et al. |
| 2010/0217234 A1 | 8/2010 | Grovender et al. |
| 2012/0065569 A1 | 3/2012 | Steegers et al. |
| 2015/0038908 A1 | 2/2015 | Antonucci |
| 2017/0259041 A1 | 9/2017 | Lenker |
| 2019/0030290 A1 | 1/2019 | Ginster |
| 2019/0038876 A1 | 2/2019 | Isaacson et al. |
| 2019/0038877 A1 | 2/2019 | Isaacson et al. |
| 2020/0188632 A1 | 6/2020 | Burkholz et al. |
| 2020/0330729 A1 | 10/2020 | Petitpierre et al. |
| 2022/0211981 A1 * | 7/2022 | Darbellay ......... A61M 25/0147 |

FOREIGN PATENT DOCUMENTS

| | | |
|---|---|---|
| JP | 2016002210 A | 1/2016 |
| WO | 2009131583 A1 | 10/2009 |
| WO | 2019081962 A1 | 5/2019 |
| WO | 2021076894 A1 | 4/2021 |

* cited by examiner

VASCULAR ACCESS WIRE TIP COMPRISING A CRANK

CROSS REFERENCE TO RELATED APPLICATIONS

This application is a continuation of International Application PCT/IB2022/057381, filed on Aug. 8, 2022.

FIELD

The present disclosure, in some embodiments thereof, relates to devices and methods for accessing a blood vessel, and more particularly, but not exclusively, to vascular access wires and/or vascular access kits.

BACKGROUND

The Seldinger technique is currently the preferred approach to access blood vessels, in which a needle penetrates into the vessel, and, once it is verified that the needle tip is inside the vessel, a vascular access wire is inserted through the needle and maneuvered to the desired place in the blood vessel, then the needle is taken out and a catheter can be positioned over the vascular access wire at the designated area.

Unintended perforation or dissection of the blood vessel is not an uncommon failure when using Seldinger technique. If the needle tip is positioned near the blood vessel centerline, and in an acute angle thereto, the vascular access wire should exit the needle tip without causing unnecessary perforation as described. However, in many cases the needle tip is too close to the opposing vessel wall, or even partly penetrated thereto, although the operator may obtain blood return via the inserted needle, supposedly a positive indication for a correct needle placement. However, the vascular access wire is pushed into the blood vessel through the needle, the tip of the vascular access wire can perforate the vessel wall and/or dissect vessel wall layers, especially since that vascular access wires are designed for sufficient pushability for allowing its advancing through the needle and the blood vessel.

The problem of unintentional penetration (e.g., perforation and/or dissection) of blood vessel wall when forming access into the blood vessel is especially noticeable in veins, in which the walls are thin and flexible, such that the operator may not sense any resistance from the needle and continue advancing the vascular access wire out of the vein through the unintentionally formed penetration opening. In arteries on the other hand, a situation of blood return with inability to advance the wire is more common. In such cases, the wire tip can be pushed directly against the vessel wall and even if it doesn't penetrate the vessel wall, it can cause dissection and/or irritation which may lead to vascular spasm commonly associated with access complications, especially vascular occlusion.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

The present disclosure, in some embodiments thereof, relates to devices and methods for accessing a blood vessel, and more particularly, but not exclusively, to vascular access wires and/or vascular access kits configured to prevent unintentional harm of blood vessel wall when forming access into a blood vessel.

In certain embodiments, there is provided a vascular access wire, comprising an elongated core member and a distal tip comprising a crank configured with a crank distal surface and a crank center of rotation. In some embodiments, the crank is configured to rotate about the crank center of rotation when the core member is sufficiently loaded axially and when the crank distal surface is pressed against a wall of a target blood vessel, for triggering or affecting a deflecting and/or a deforming of the core member proximally to the crank.

In some embodiments, the deflecting and/or deforming includes buckling, bending and/or rotating.

In some embodiments, the crank distal surface is curved, and the crank center of rotation coincides with a center of curvature of the crank distal surface or is adjacent thereto. In some embodiments, the crank distal surface has a crank radius of curvature within a range of 0.1 mm to 0.5 mm, optionally particularly about 0.25 mm.

In some embodiments, the core member includes, or merges with the distal tip through, a hinge configured to facilitate and/or allow articulation of the crank thereabout for converting an axial motion of the core member to a rotational motion of the crank and/or for converting a rotational motion of the crank to an axial motion of the core member. In some embodiments, a distance of the hinge from the crank center of rotation is smaller than diameter of the blood vessel. In some embodiments, the distance of the hinge from the crank center of rotation is equal to or smaller than about 2 mm, or optionally particularly equal to or smaller than about 1 mm. In some embodiments, the hinge is configured as a flexing portion of the core member and includes a curved length along which the core member is fixedly deviated laterally relatively to straight aligned portions of the core member proximally and distally adjacent to the curved length. In some embodiments, the flexing portion is about 0.5 mm or less in length.

In some embodiments, the vascular access wire is configured such that the crank is prevented from rotating about the crank center of rotation when the core member is axially loaded with a first axial force smaller than a predetermined compression force and/or such that the crank is forced to rotate about the crank center of rotation when the core member is axially loaded with a second axial force greater than the predetermined compression force. In some embodiments, the predetermined compression force is within a range of 0.1 N to 2 N, optionally particularly within a range of 0.2 N to 0.8 N.

In some embodiments, the vascular access wire further comprising a cylindrical coil member extending longitudinally around a length of the core member. In some embodiments, the distal tip fixedly joining distal ends of the core member and of the coil member. In some embodiments, the distal tip is formed by way of welding and/or fusing together portions of the core member and the coil member. In some embodiments, the distal tip includes most or all heat-affected zone resulted from the welding and/or fusing.

In some embodiments, the distal tip includes a spherical-dome-shaped portion having a distally pointing apex.

In some embodiments, the core member includes a slender segment extending between a proximal widened segment and distal widened segment, such that the deflecting and/or the deforming is subjected to occur in the slender segment. In some embodiments, the slender segment includes, or merges with the distal widened segment through, a hinge configured to facilitate and/or allow articulation of the crank thereabout for converting between a rotational motion of the crank and a linear motion of the core member. In some embodiments, the distal widened segment merges with the distal tip at a distal merging portion. In some embodiments, a volume ratio between a total volume of the distal tip and a total volume of the distal widened segment is greater than 1.3. In some embodiments, the total volume of the distal tip is within a range of 0.2 mm^3 to 0.5 mm^3, and/or the total volume of the distal widened segment is within a range of 0.005 mm^3 to 0.03 mm^3. In some embodiments, a length ratio between a total length of the distal tip and a total length of the distal widened segment is within a range of 1 to 2. In some embodiments, the total length of the distal tip is about 0.35 mm or less, and/or the total length of the distal widened segment is about 0.75 mm or less. In some embodiments, the slender segment and/or the distal widened segment is elongated and has a circular, an elliptical, or a rectangular cross section. In some embodiments, the coiled member is configured with coil pitch greater along the slender segment than along the distal widened segment.

In certain embodiments there is provided a vascular access kit comprising the vascular access wire and a needle comprising a beveled opening. In some embodiments, the hinge is positioned along the beveled opening when the distal end of the vascular access wire is in juxtaposition with a distal end of the needle.

In certain embodiments there is provided a method of forming a vascular access using the vascular access kit. The method may comprise: penetrating into a blood vessel with the beveled opening; pushing the distal tip of the vascular access wire via the beveled opening against a wall of the blood vessel until generating rotational motion of the crank about the crank center of rotation sufficient to trigger and/or affect deflecting and/or a deforming of the core member proximally to the crank, and/or sufficient to trigger or affect articulation of the crank about the hinge. In some embodiments, the method further comprising advancing the vascular access wire distally in the blood vessel, and allowing the core member to flex back and/or realign with the distal tip.

In certain embodiments, there is provided a method of producing the vascular access wire. The method may comprise joining a distal end of the core member and a distal end of the coil member, and forming the hinge. In some embodiments, the forming includes, or is caused by, fixedly altering a straight aligned length of the core member. In some embodiments, the forming includes, or is caused by, fixedly deforming a portion of the core member into a curved length.

In some embodiments, the forming includes pushing the core member along a chosen pushing axis against a surface perpendicular to the pushing axis. In some embodiments, the pushing is performed while a chosen unsupported length of core member is allowed to buckle or bend transversely to the pushing axis and a supported length of core member proximally to the unsupported length is prevented from buckling or bending transversely to the pushing axis. In some embodiments, a portion of the distal tip is prevented from shifting transversely to the pushing axis and/or is supported in a niche surrounded by the surface.

In some embodiments, the method further comprising shaping the distal tip. In some embodiments, the forming follows the joining and/or the shaping. In some embodiments, the joining includes, or results in, the shaping. In some embodiments, the distal tip shaped into forming the crank which includes a spherical-dome-shaped portion having a distally pointing apex. In some embodiments, the shaping includes shaping a pre-shaped tip into the distal tip. In some embodiments, the joining includes welding and/or fusing together pre-fused portions of the core member and the coil member. In some embodiments, the pre-fused portions are configured to form a weld pool for facilitating the welding and/or fusing. In some embodiments, the distal tip is configured to sustain most or all heat-affected zone resulting from the welding and/or fusing, such that the core member adjacent to the hinge is structurally and/or functionally unaffected by the welding and/or fusing All technical or/and scientific words, terms, or/and phrases, used herein have the same or similar meaning as commonly understood by one of ordinary skill in the art to which the disclosure pertains, unless otherwise specifically defined or stated herein. In case of conflict, the patent specification, including definitions, will control.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Some embodiments of the present disclosure are herein described, by way of example only, with reference to the accompanying drawings. With specific reference now to the drawings in detail, it is stressed that the particulars shown are by way of example and for purposes of illustrative description of some embodiments of the present disclosure. In this regard, the description taken together with the accompanying drawings make apparent to those skilled in the art how some embodiments of the present disclosure may be practiced.

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

The present disclosure, in some embodiments thereof, relates to devices and methods for accessing a blood vessel, and more particularly, but not exclusively, to vascular access wires and/or vascular access kits configured to prevent unintentional harm (e.g., puncture) of blood vessel wall when forming access into a blood vessel. The term "vascular access wire" (or "guide wire") refers to any thin member configured for facilitating a chosen route in bodily vessels for passing artifacts therealong to a target location, such as by way of passing a sheath, a cannula, a catheter or any other device over the vascular access wire into a cavity or vessel. In some embodiments, the term vascular access wire is inclusive of vascular access wires which are used in the process of forming a vascular access, optionally prior to insertion of another vascular access wire prescribed for routing artifacts deeper in the patient's vasculature, for example.

Figure 1A:
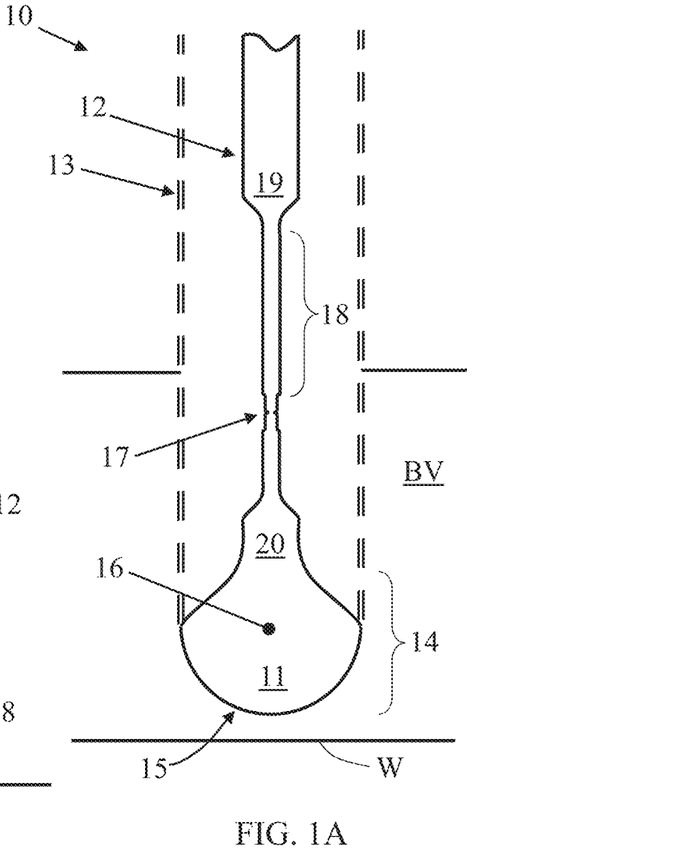
FIGS. 1A-1B schematically illustrate, respectively, side cross sectional views of an exemplary vascular access wire comprising a crank, before and after forcing the crank into rotational motion, according to some embodiments.
Figure 1B:
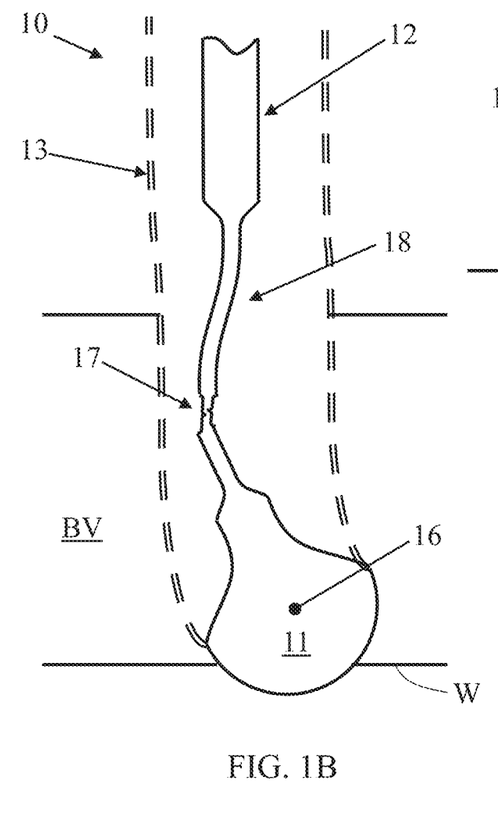

FIGS. 1A-1B schematically illustrate, respectively, side cross sectional views of an exemplary vascular access wire 10 comprising a crank 11, before and after forcing the crank into rotational motion. As used herein, the term "crank" refers to a mechanism, a member or a portion of vascular access wire, configured for and/or capable of rotating when pushed against a surface. When extending from or connected to an axial member via a sufficiently flexible portion or a joint (e.g., a hinge), a linear motion of the axial member can be converted to a rotational motion of the crank and/or a rotational motion of the crank can be converted to a linear motion of the axial member.

Vascular access wire 10 includes an elongated core member 12, a cylindrical coil member 13 extending longitudinally around a length of core member 12. A distal tip 14 extends distally from core member 12, and may be considered a distal part thereof or connected, joined, or merging thereto. Distal tip 14 includes crank 11 that is configured with a crank distal surface 15 and a crank center of rotation 16. Crank distal surface 15 may be curved, as shown, and crank center of rotation 16 may coincide with a center of curvature of crank distal surface 15 or be adjacent thereto. Crank 11 is configured to rotate about crank center of rotation 16 when core member 12 is loaded axially (e.g., by way of pushing against a resisting surface, for example) and when crank distal surface 15 is pressed against a wall W of a target blood vessel BV, sufficiently for triggering or affecting a deflecting and/or a deforming (e.g., buckling, bending and/or rotating) of core member 12 proximally to crank 11. In some embodiments, crank distal surface 15 has a crank radius of curvature within a range of 0.1 mm to 0.5 mm, optionally particularly about 0.25 mm.

Core member 12 includes, or merges with distal tip 14 through, a hinge 17 which is configured to facilitate and/or allow articulation of crank 11 thereabout for converting a linear motion of the core member to a rotational motion of the crank and/or for converting a rotational motion of the crank to a linear motion of the core member. The distance of hinge 17 from crank center of rotation 16 is smaller than diameter of blood vessel BV, so as to allow the deflecting or the deforming of core member 12 resulting from rotation of crank 11. In some embodiments, the distance of hinge 17 from the crank center of rotation 16 is equal to or smaller than about 5 mm or than about 2 mm, or may optionally be equal to or smaller than about 1 mm for forming access in substantially small blood vessels such as small peripheral veins. Hinge 17 may be configured as a flexing portion of core member 12, in some such embodiments it may include a curved length along which core member 12 is fixedly deviated laterally relatively to straight aligned portions thereof proximally and distally adjacent to the curved length. In some such embodiments, the flexing portion is about 0.5 mm or less in length.

Vascular access wire 10 is configured such that crank 11 is prevented from rotating about crank center of rotation 16 when core member 12 is axially loaded with a first axial force smaller than a predetermined compression force and/or such that crank 11 is forced to rotate about the crank center of rotation 16 when core member 12 is axially loaded with a second axial force greater than the predetermined compression force. This can be achieved for example by considering mechanical, static and dynamic, design aspects such as resistance to bending of core member 12, resistance to rotating of hinge 17, moment of inertia and/or radius of curvature of hinge 17, and/or distance between hinge 17 and crank center of rotation 16, for example. In some such embodiments, the predetermined compression force is optionally taken within a range of 10 gr to 200 gr, optionally particularly within a range of 20 gr to 80 gr. In some embodiments, the predetermined compression force can be predetermined (e.g., preset) in accordance with mechanical and physiological features of the blood vessel BV, and for example it may be limited so as to prevent damage or to penetrate through blood vessel wall W.

In some embodiments, distal tip 14 fixedly joins distal ends of core member 12 and of coil member 13. Distal tip 14 is optionally formed by way of welding and/or fusing together portions of core member 12 and coil member 13. In some such embodiments, distal tip 14 includes most or all heat-affected zone resulted from the welding and/or fusing. Distal tip 14 may include a spherical-dome-shaped portion having a distally pointing apex, which may be shaped as such using a selected shaping process or as a direct result from the welding and/or fusing technique or instrumentation used.

Core member 12 may include a slender segment 18 extending between a proximal widened segment 19 and distal widened segment 20, such that any deflecting and/or the deforming is subjected to occur in slender segment 18. Slender segment 18 may include, or it may merge with distal widened segment 20 through, hinge 17. A volume ratio between a total volume of distal tip 14 and a total volume of distal widened segment 20 is optionally greater than 1, optionally greater than 1.3, or optionally greater than 1.5. The total volume of distal tip 14 is optionally taken within a range of 0.1 mm^3 to 1 mm^3, optionally particularly within a range of 0.2 mm^3 to 0.5 mm^3. The total volume of distal widened segment 20 is optionally taken within a range of 0.001 mm^3 to 0.1 mm^3, optionally particularly within a range of 0.005 mm^3 to 0.03 mm^3. A length ratio between a total length of distal tip 14 and a total length of distal widened segment 20 is optionally within a range of 0.5 to 5, optionally particularly within a range of 1 to 2. The total length of distal tip 14 is optionally about 1 mm or less, optionally about 0.5 mm or less, or optionally particularly about 0.35 mm or less. The total length of distal widened segment 20 is optionally about 1 mm or less, or optionally particularly about 0.75 mm or less. Slender segment 18, proximal widened segment 19 and/or distal widened segment 20 is optionally elongated and has a circular, an elliptical, or a rectangular cross section. Coiled member 13 is optionally configured with coil pitch greater along slender segment 18 than along other portions of core member 12, such as particularly along distal widened segment 20.

FIG. 11A shows a scenario in which vascular access wire 10 has penetration with a distal portion thereof into blood vessel BV and before reaching wall W with crank 11. FIG. 1B shows a second scenario in which wire 10 is pushed against blood vessel wall W with crank 11 presses it. As shown, after an initial contact and sufficient axial force applied to wire 10, crank 11 has rotated to one side (in this example, counterclockwise) around center of rotation 16, thereby triggering or affecting bending or flexing of core member 12 about hinge 17. Such rotational motion of crank 11 and flexing of hinge 17, while wire 10 is continuously pushed distally towards blood vessel wall W, can cause deflecting and/or deforming of slender segment 18 proximally and/or adjacent to hinge 17. In some embodiments, flexing of 17 and/or deformation of slender segment 18 is elastic and fully or substantially recoverable so that core member 12 can be substantially aligned once stresses are no longer applied thereto.

Figure 2A:
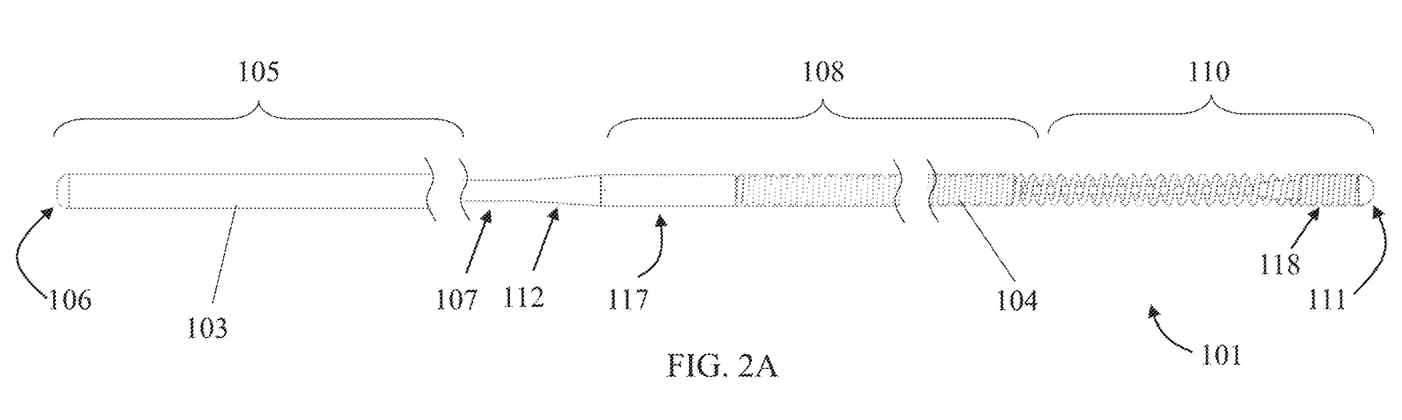
FIGS. 2A-2B illustrate respectively a side view of an exemplary vascular access wire and a cross-sectional side view of a front length thereof, according to some embodiments.
Figure 2B:
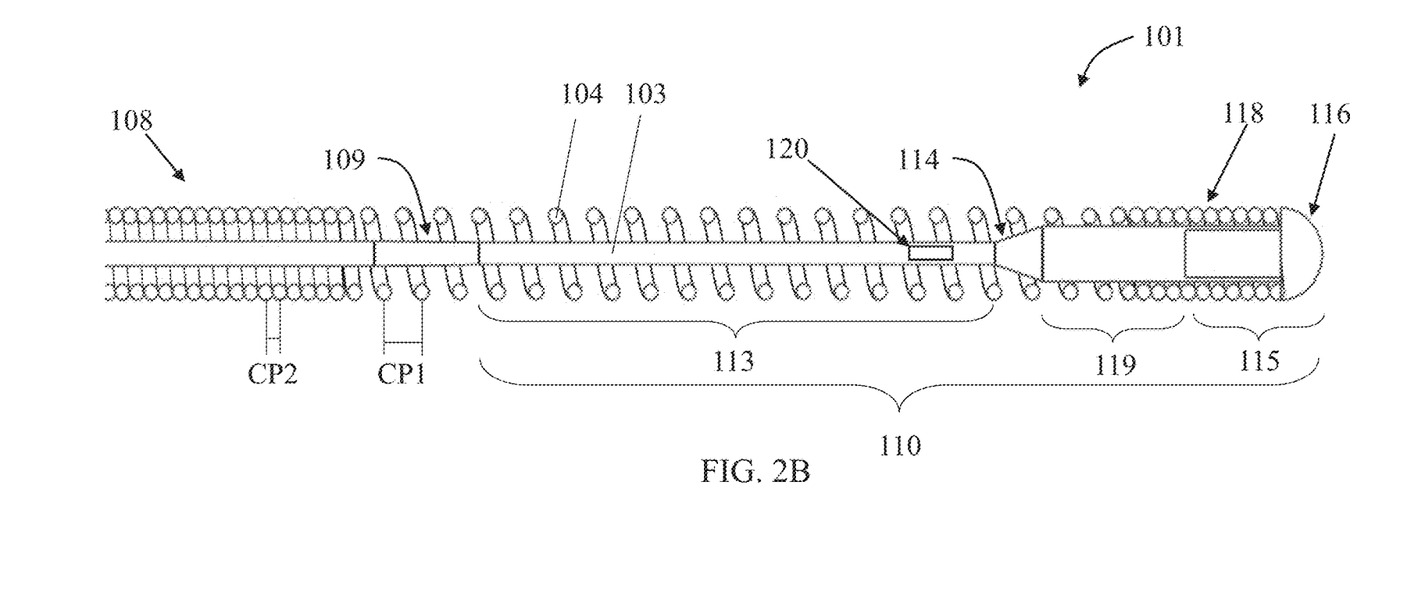

FIGS. 2A-2B illustrate respectively side view of a vascular access wire 101 and a cross-sectional side view of a front length thereof. Vascular access wire 101 is optionally similar or identical at least in part to vascular access wire 10, optionally as an exemplary configuration thereof. Vascular access wire 101 includes an elastic core member 103, optionally made from an elastic or a super elastic material (e.g., formed of Ni—Ti alloy, for example), which extends along most or all length of the vascular access wire. Vascular access wire 101 further includes a coil member 104 covering core member 103 along part of its length. Core member 103 includes three main continuous segments which are distinguishable by functional, structural and/or dimensional characteristics: (1) a vascular access wire proximal segment 105 extending distally from a proximal end 106 of vascular access wire 101 to a first narrowing 107 of core member 103, (2) a vascular access wire intermediate segment 108 extending distally from first narrowing 107 to a proximal widened segment 109 of core member 103, and (3) a vascular access wire tip segment 110 extending distally from proximal widened segment 109 to a distal end 111 of vascular access wire 101.

Similar to other access vascular access wires configured for forming intravenous access, such as for inserting sheaths or lines, total length of vascular access wire 101 can be in the order of 500 mm, optionally about 450 mm, for example. Vascular access wire proximal segment 105 can be about 80% or more of total length of vascular access wire 101, optionally about 375 mm, and is indicated with a substantially constant diameter (optionally about 0.45 mm) and/or with having core member 103 uncovered with coil member 104, along most or all length thereof. Vascular access wire intermediate segment 108 can be in the order of 10% or 15% of vascular access wire 101 total length, for example, optionally about 45 mm. Vascular access wire intermediate segment 108 is optionally formed in a slender elongated frustum-like shape which narrows (in proximal to distal direction) continuously and/or stepwise along most or all length thereof, from first narrowing 107 to proximal widened segment 109. First narrowing 107 optionally may be in the order of 1%, 2% or 5% of vascular access wire 101 total length, and proximal widened segment 109 is optionally steeper than inclined length of first narrowing 107 and/or of vascular access wire intermediate segment 108, optionally a drop or an inclination of about 10% or more in diameter along a length of about 0.5 mm. Optionally, a short proximal widening 112 is formed between first narrowing 107 and vascular access wire intermediate segment 108 for example due to bonding of coil member 104 to core member 103 thereto.

Vascular access wire tip segment 110 is considerably shorter than the other segments and is about 2% or less (optionally in the order of 1%) of the total length of vascular access wire 101, optionally less than 10 mm, optionally about 5 mm or less. Vascular access wire tip segment 110 includes a slender segment 113 and a distal widened segment 119 which merge together with a local (distal) widening 114 of core member 103. Vascular access wire tip slender segment 113 merges to vascular access wire intermediate segment 108 with proximal widened segment 109 and it is optionally the thinnest portion of core member 103, having a constant and/or average diameter that is in the order of 30% or less of vascular access wire 101 maximal diameter, optionally less than 0.15 mm, optionally about 0.1 mm for example, along a length of about 6 mm or less or of about 3 mm or less. Widening 114 is steep and optionally increases by more than twice in diameter (e.g., from about 0.1 mm to more than 0.25 mm for example) along a minimal length such as in the order of about 0.5 mm or 0.25 mm. Unlike first narrowing 107 and proximal widened segment 109 that are formed in an acute angle, widening 114 is optionally formed in an obtuse angle. Vascular access wire tip segment 110 includes a distal tip 115 comprising a dome-like shaped crank 116. Distal tip 115 includes a proximal portion which is about 0.25 mm or more in diameter and about 1.5 mm or less in length. Crank 116 is optionally about 0.23 mm in radius and length. Crank 116 is configured to rotate about its center of rotation when core member 103 is loaded axially and while crank's distal surface is pressed against a wall of a target blood vessel, sufficiently for triggering or affecting a deflecting and/or a deforming of core member 103 proximally thereto.

Vascular access wire tip slender segment 113 includes a hinge 120 that is configured to facilitate and/or allow articulation of crank 116 thereabout for converting an axial motion of core member 103 to a rotational motion of crank 116 and/or for converting a rotational motion of crank 116 to an axial motion of core member 103. Hinge 120 is optionally formed of a flexing portion of core member 103, along slender segment 113 or adjacently thereto. Hinge 120 may be mechanically and/or thermally treated, such as in a material subtraction process, for producing a localized smaller resistance to buckling, flexing and/or bending and/or for affecting a geometric misalignment sufficient for causing a pivot point or area for such an inclination or articulation. In some embodiments, hinge 120 has elastic properties configured for affecting self-aligning of distal widened segment 119 with vascular access wire tip slender segment 113 upon ceasing of a moment thereon. Hinge 120 is optionally about 1 mm or less, optionally about 0.5 mm or less, in length; and it is optionally 5 mm or less distant from vascular access wire distal end 111 and/or optionally 1 mm or less distant from distal widened segment 119.

Coil member 104 is optionally cylindrical with a constant outer diameter along most or all length thereof and is configured to maintain a constant vascular access wire maximal outer diameter (e.g., about 0.45 mm, for example) around narrowed portions of core member 103 including around vascular access wire intermediate segment 108 and vascular access wire tip segment 110. Coil member 104 is connected with a proximal portion 117 thereof to a proximal portion of vascular access wire intermediate segment 108 in proximity to first narrowing 107 optionally thereby forming proximal widening 112 (shown embedded in adhesive layer, which is an exemplary connecting feature), and with a distal portion 118 thereof to distal tip 115 of distal widened segment 119. In some embodiments, coiled member 104 is configured with a first coil pitch CP1 along vascular access wire tip slender segment 113 (optionally particularly over hinge 120) which is greater than a second coil pitch CP2 thereof provided along vascular access wire intermediate segment 108 and distal widened segment 119 (and optionally also over portions of vascular access wire tip slender segment 113 other than hinge 120). In other embodiments, coil member 104 is configured with first (greater) coil pitch CP1 along other portions thereof, such as along vascular access wire intermediate segment 108 and/or distal widened segment 119, or along most or all length thereof. In some embodiments, second coil pitch CP2 substantially equals the diameter of the coil-wire (the wire forming the coil; which may be about 0.08 mm or less, for example) such that each two adjacent coil winding is in contact or near contact, thereby resisting or preventing axial contraction and/or bending. First coil pitch CP1 is optionally greater than coil-wire diameter (e.g., more than 0.09 mm for example) thereby allowing axial contraction and/or bending and configured to facilitate inclination of distal widened segment 119 relative to vascular access wire tip slender segment 113.

Vascular access wire 101 is formed by first producing separately core member 103 and coil member 104, and then connecting them as described. Core member 103 is first formed by material subtraction of a pre-machined wire (i.e., having a substantially constant diameter), such as by way of grinding (e.g., using spindle-axis grinding in which the wire is concentrically aligned to machine's spindle axis and grinded while maintaining cylindrically symmetric shape), to reach a chosen shape of core member 103, including along each one of first narrowing 107, vascular access wire intermediate segment 108, second narrowing 114, vascular access wire tip slender segment 113, widening 114, and distal widened segment 119. Afterwards, a portion having a chosen length and location on vascular access wire tip slender segment 113 can treated to form hinge 120. This may include fixedly altering a straight aligned length of vascular access wire tip slender segment 113 to thereby form the flexing portion. Additional chemical or heat treatment may be needed. Fixedly altering the straight aligned length to form hinge 120 may include fixedly deforming it into a curved length, along which core member 103 is fixedly deviated laterally relatively to straight aligned portions thereof proximally and distally adjacent to the curved length. Alternatively or additionally, this process may include forming at least one lateral recess or slit from the straight aligned length by way of subtractive manufacturing, such as by using a laser source or by way of off-spindle-axis (eccentric) grinding (e.g., the grinded wire is fixated parallel and transversely to spindle axis). After forming flexing portion, coiled member 104 is sleeved over core member 103 and positioned such that vascular access wire tip slender segment 113 is surrounded with the length of coiled member 104 configured with first coiled pitch CP1. In some embodiments, proximal portion 117 of coiled member 104 may be connected to core member 103 by of adhesives, and distal portion 118 thereof may be welded or soldered to distal tip 115 of distal widened segment 119. During or following connection of coiled member distal portion 118, the dome-like shaped crank 116 of distal widened segment 119 can be connected (e.g., welded or soldered, for example) or formed from the tip of core member 103 (e.g., grinded or forged, for example).

Figure 3A:
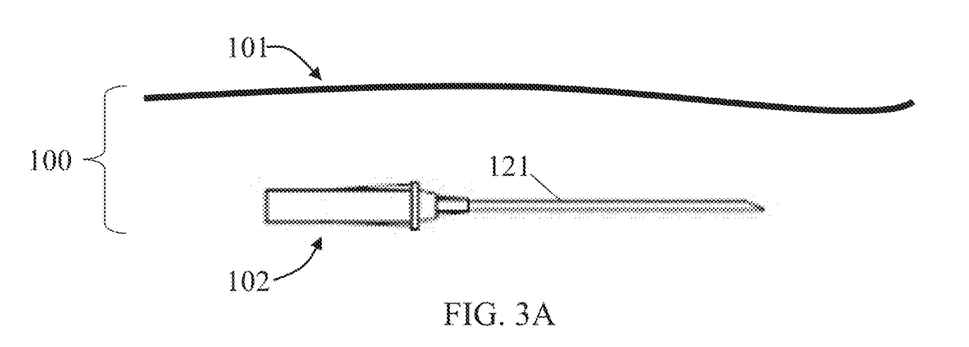
FIG. 3A illustrates an exemplary intravenous access kit comprising an exemplary needle and the vascular access wire shown in FIG. 2A, according to some embodiments.
Figure 3B:
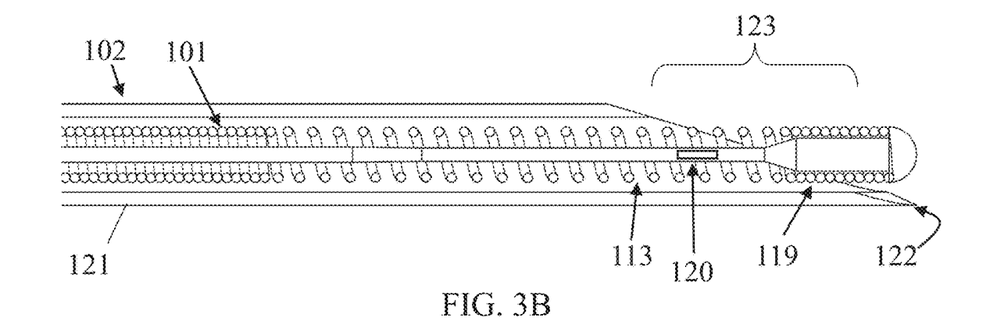
FIG. 3B illustrates a cross-sectional side partial view of the intravenous kit shown in FIG. 3A in an exemplary deployment, according to some embodiments.

FIG. 3A illustrates an exemplary vascular access kit 100 comprising vascular access wire 101 and an exemplary needle 102. FIG. 3B illustrates a cross-sectional side view showing distal portions of vascular access wire 101 placed in an exemplary needle 102. Kit 100 may be a complete or partial seldinger or other vascular access or puncture kit, and may include other instruments such as a syringe, an introducer sheath and/or a dilator, and it may be equipped with one or more types or sizes of vascular access wire 101 and/or needle 102. Needle 102 is optionally similar or identical at least in part to needle 20 or needle 60, optionally as an exemplary configuration thereof. Needle 102 includes a hollow tube 121 sized to accommodate unhindered passage of vascular access wire 101 therethrough. Needle hollow tube 121 ends with a needle tip 122, configured to facilitate initial penetration through skin layers and through blood vessel walls in a live subject, and a beveled opening 123 ending at needle tip 122. The length of beveled opening 123, taken parallel to centerline of needle hollow tube 121, is greater than length of distal widened segment 119 and optionally also of additional length of vascular access wire 101, such that in some embodiments some, most or all length of vascular access wire tip slender segment 113, including total length of hinge 120, extends along beveled opening 123, when distal ends/tips of vascular access wire 101 and needle 102 are juxtapositionally aligned, as shown in FIG. 3B. This way, when vascular access wire 101 is pushed through needle 102 against a surface common to both (i.e., both are in contact with or adjacent thereto), such as against a blood vessel wall, needle 102 does not constrain hinge 120 and allows localized bending and/or flexing for affecting inclination of distal widened segment 119 relative to vascular access wire tip slender segment 113. In some embodiments, beveled opening 123 is at least twice in length than distal widened segment 119, and is optionally at least 2 mm, optionally at least 4 mm, or optionally at least 6 mm long, or higher, or lower, or of any intermediate value.

Figure 3C:
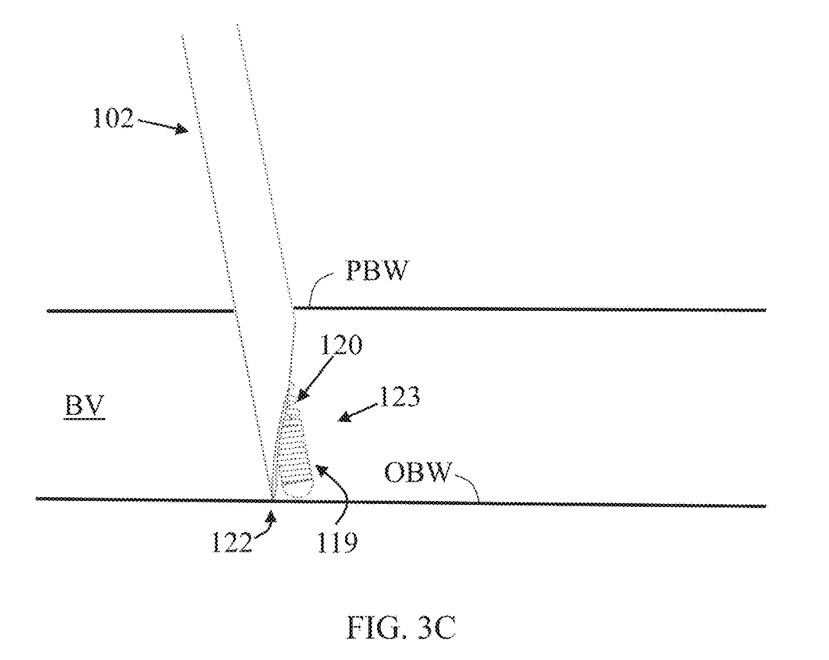
FIG. 3C schematically illustrates a view representing a possible scenario in execution of a method forming an intravenous access using the kit of FIG. 3A, according to some embodiments.

As shown in FIG. 3C, needle 102 is penetrated into blood vessel BV such that beveled opening 123 is completely in the blood vessel lumen. In common practice, practitioners try to penetrate veins in most shallow angle possible, or to rotate the needle to a shallow angle immediately upon initial penetration, in order to diminish potential harm of unintentional penetration of the second (inferior) blood vessel wall by the needle tip and/or the vascular access wire. However, by introducing kit 100 with the tip-articulatable vascular access wire 101 unbound by beveled opening of needle 102, practitioners may penetrate blood vessels in less acute angles such as between 60° and 90°.

Figure 4A:
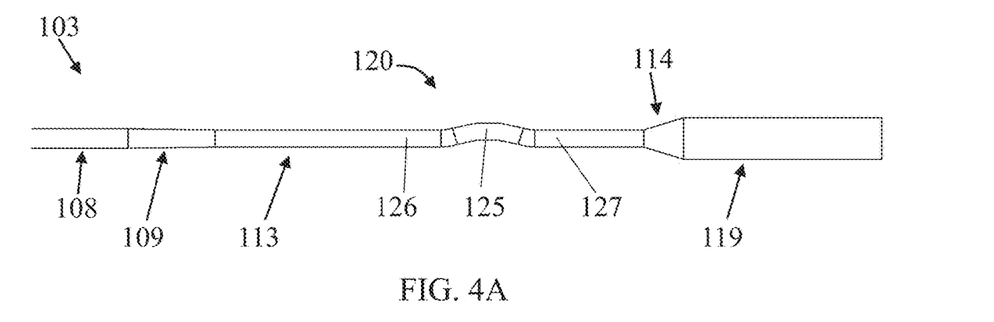
FIGS. 4A-4C illustrate respectively side views of distal portions of exemplary vascular access wire core member with different exemplary flexing portion configurations, according to some embodiments.
Figure 4B:
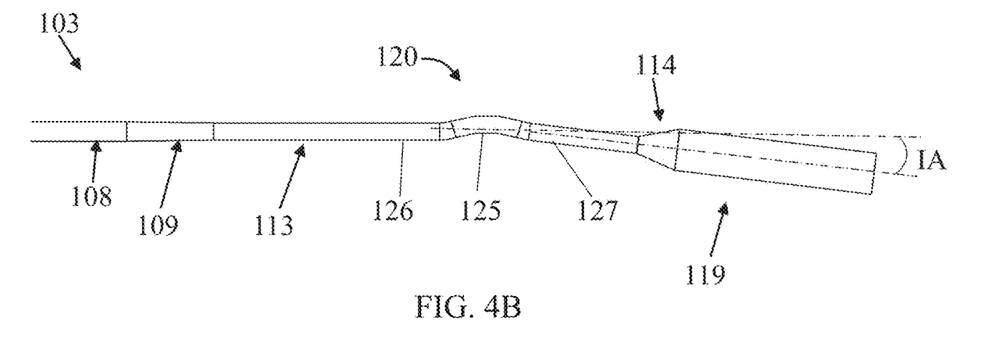
Figure 4C:
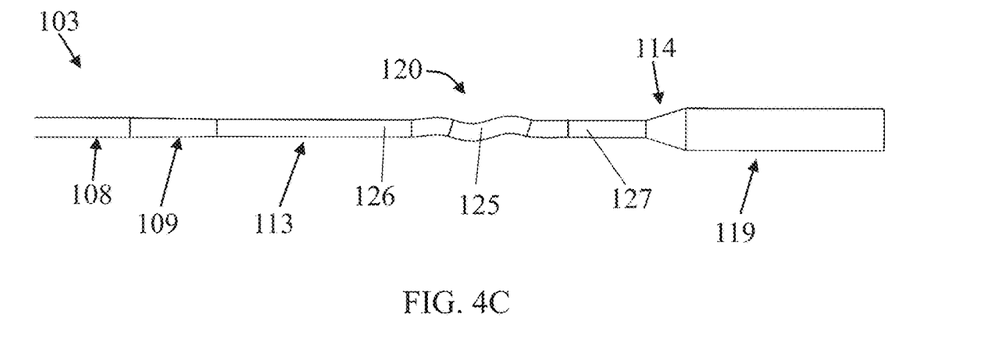

FIGS. 4A-4C illustrate respectively side views of distal portions of exemplary configurations of core member 103

(without or prior to shaping of distal tip 115 and/or forming crank 116), differentiated with exemplary configurations of hinge 120. In some embodiments, exemplary configurations described herein are intended for causing (affecting) localized buckling and/or bending of vascular access wire tip slender segment 113 along or in proximity to hinge 120, when core member 103 undergoes axial compression such as when pushed with forces equal to smaller than forces normally used to push access wires via access needle. Exemplary normal pushing and/or axial compression force on the vascular access wire sufficient to cause such buckling, bending and/or inclination in vascular access wire 101 are optionally lower than 2 N (newton), optionally about 1 N or less, optionally about 0.75 N or less, optionally about 0.5 N or less, optionally about 0.2 N or less, optionally about 0.1 N or less. This will allow or generate inclination of distal widened segment 119 relative to vascular access wire tip slender segment 113 also when distal widened segment 119 fully resides within beveled opening 123 of needle 102. With such configurations the aim is to avoid common failures associated with known access vascular access wires and kits with which such buckling, bending and/or inclination is constrained and prevented by the needle when the vascular access wire is pushed with normal forces, thereby increasing potential to harm blood vessel wall such as by way of unintentional puncture and/or dissection.

FIG. 4A shows vascular access wire 101 having a first configuration of hinge 120, in which hinge 120 includes a curved length 125 along which core member 103 is fixedly deviated laterally relatively to straight aligned portions 126 and 127 of core member 103 proximally and distally adjacent to curved length 125. In this configuration, core member 103 is deviated in a transverse axis (relative to the long axis) along curved length 120. As such, hinge 120 causes a local smaller resistance to buckling and/or bending along curved length 125 than along straight aligned portions 126 and 127, when core member 103 undergoes axial compression. FIG. 4B shows a similar configuration of hinge 120 to the previous configuration of FIG. 4A, in which length of core member 103 distal to curved length 125 is fixedly inclined at an inclination angle IA relative to length of core member 103 proximal to curved length 125. Inclination angle IA is optionally smaller than about 20°, optionally smaller than about 10°, optionally smaller than about 5°, or have any intermediate value. FIG. 4C shows vascular access wire 101 having a second configuration of hinge 120, in which hinge 120 forms a coil along curved length 125. In this configuration, core member 103 is deviated in several axes along curved length 120 and can compress axially under axial loads. As such, hinge 120 is configured with smaller resistance to buckling and/or bending along curved length 125 than along straight aligned portions 126 and 127 in any direction, when core member 103 undergoes axial compression.

Figure 5A:
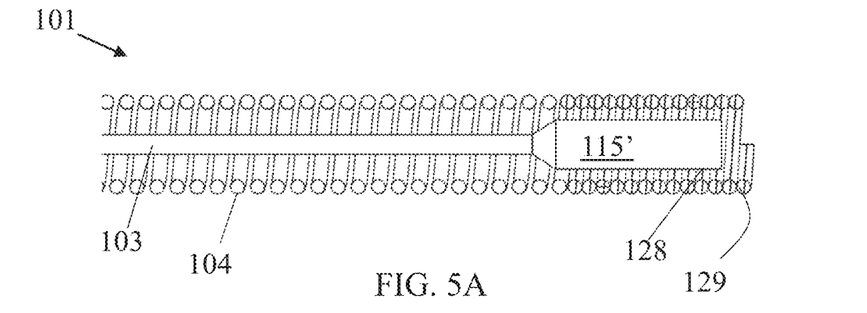
FIGS. 5A-5C illustrate, respectively, a side cross-sectional view of a distal portion of an exemplary vascular access wire before welding and shaping distal tip thereof, a side cross-sectional view and a side view of the distal portion after welding and shaping the distal tip, according to some embodiments.
Figure 5B:
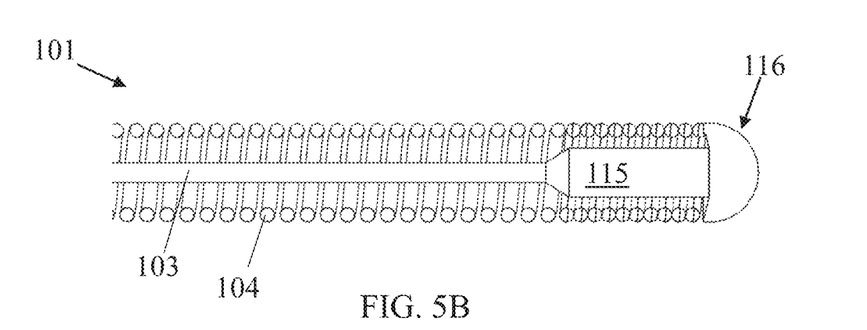
Figure 5C:
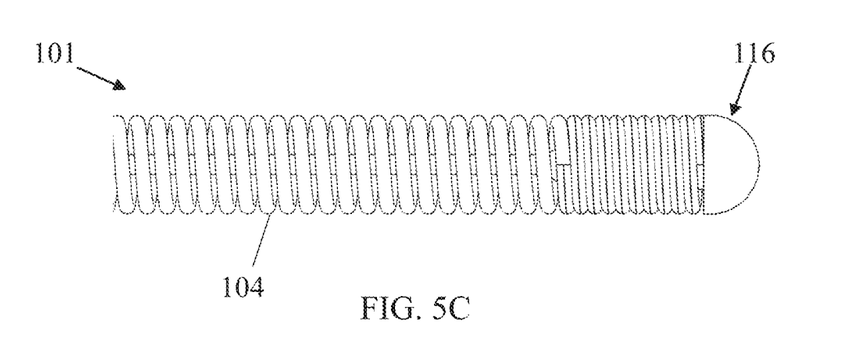

FIGS. 5A-5C illustrate, respectively, a side cross-sectional view of a distal portion of vascular access wire 101 having a pre-shaped tip 115' before welding and shaping distal tip 115 (FIG. 5A), a side cross-sectional view (FIG. 5B) and a side view (FIG. 5C) of the distal portion after welding and shaping distal tip 115. As shown, coil member 104 is sleeved over core member 103 and a distal end 128 of core member 103 is put in juxtaposition with distal end 129 of coil member 104. Distal ends 128 and 129 are then joined together as a single part forming distal tip 115, such as by way of welding, soldering and/or fusing (e.g., fuse-welding) together pre-fused portions of core member 103 and coil member 104. The welding and/or fusing includes or is followed by shaping the distal tip 115 by melting pre-shaped tip 115' and cooling or allowing it to cool in the new shape which includes crank 116 having a spherical-dome-shaped portion having a distally pointing apex. In some embodiments, the pre-fused portions are configured to form a weld pool for facilitating the welding and/or fusing, and pre-shaped tip 115' and/or distal tip 115 is configured to sustain most or all heat-affected zone resulting from the welding and/or fusing, such that core member 103 adjacent to hinge 120 (before or after it is formed) is structurally and/or functionally unaffected by the welding and/or fusing.

Figure 6:
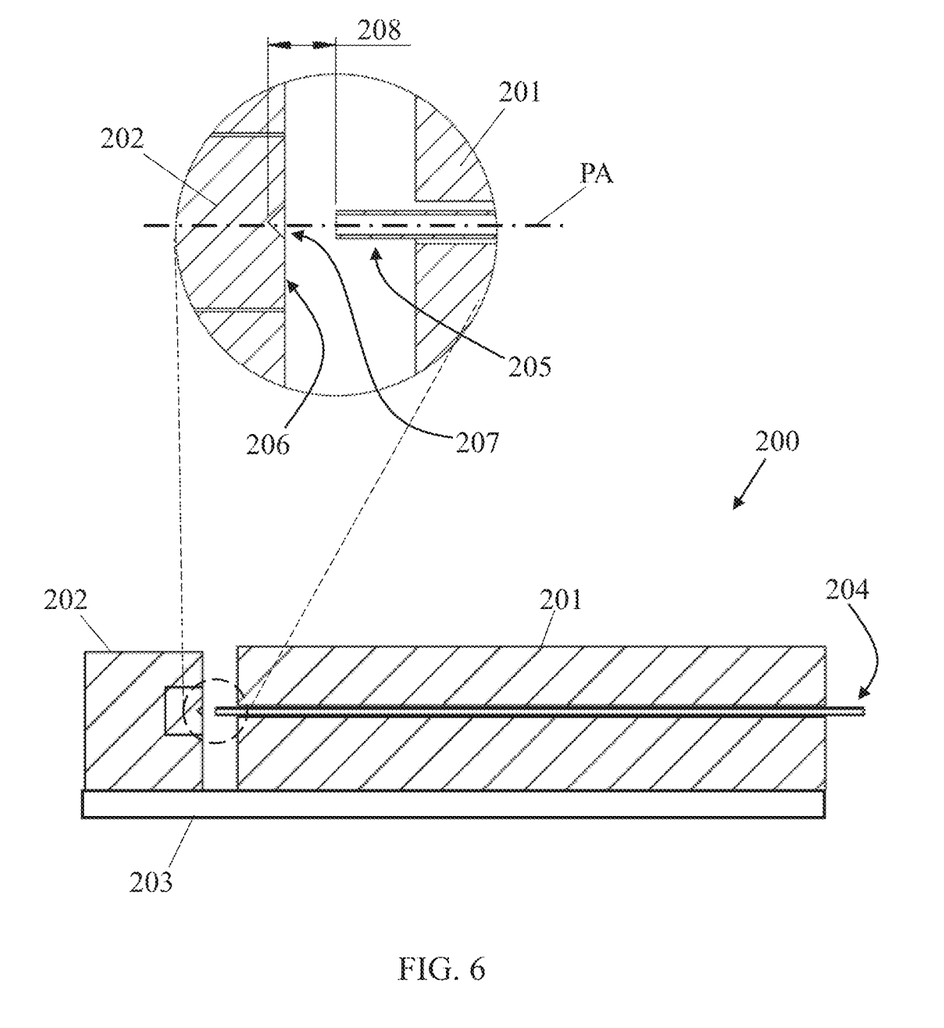
FIG. 6 illustrates a side cross-sectional view of an exemplary fixture configured for forming a hinge in a core member of an exemplary vascular access wire, according to some embodiments.

FIG. 6 illustrates a side cross-sectional view of an exemplary fixture 200 configured for forming a hinge (as a flexing portion) in vascular access wires, for example hinge 120 in core member 103. Fixture 200 includes a rigid body 201, an anvil 202 and a base 203. Rigid body 201 and anvil 202 are fixedly connected to base 203 with a fixed space therebetween, and base 203 is capable of being fixedly connected in-place. Rigid body 201 has an elongated passage extending from its rear to its front side. A rigid channel 204 (e.g., in a form of a straight cannula or a pipe) is held fixedly in and along the passage of rigid body 201, such that a front channel portion 205 emerges from the front side of rigid body 201. Rigid channel 204 is cylindrical and sized to accommodate therethrough wires like vascular access wire 101, and includes a central axis that coincides with a pushing axis PA, along which wires can be pushed through rigid channel 204. Anvil 203 has a surface 206 that is perpendicular to pushing axis PA. Surface 206 surrounds a niche 207 located directly in front of front channel portion 205 with central axis thereof also coinciding with pushing axis PA. An unsupported distance 208 between inner-most cavity of niche 207 and tip of front channel portion 205 is chosen in accordance with the preferred location of hinge 120 relative to distal tip 115, for example. In some such embodiments, unsupported distance 208 is about 5 mm or less, or optionally about 3 mm or less, or optionally about 2 mm or less.

Figure 7A:
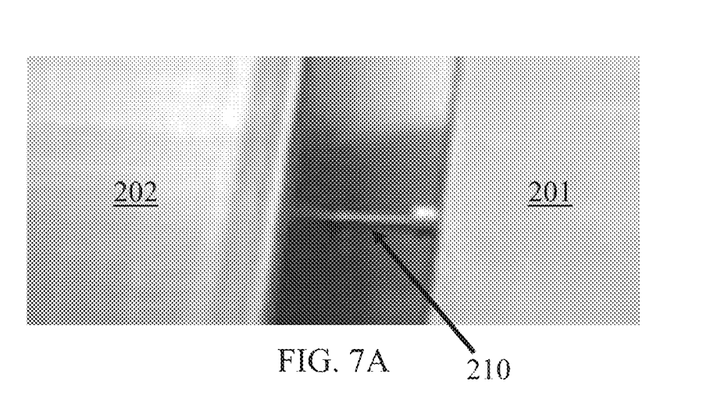
FIGS. 7A-7C show sequential frames visualizing a distal portion of an exemplary vascular access wire in an exemplary process of forming a hinge, according to some embodiments.
Figure 7B:
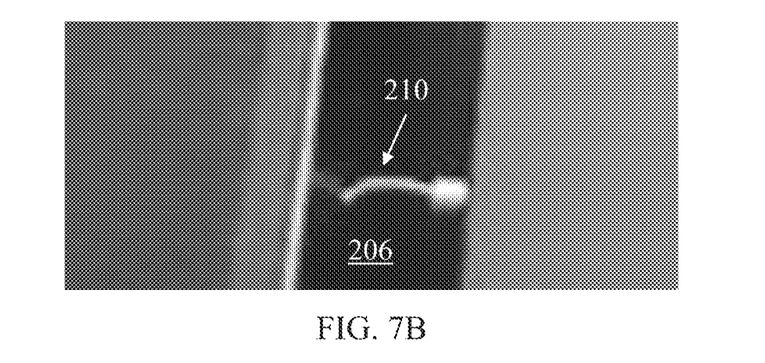
Figure 7C:
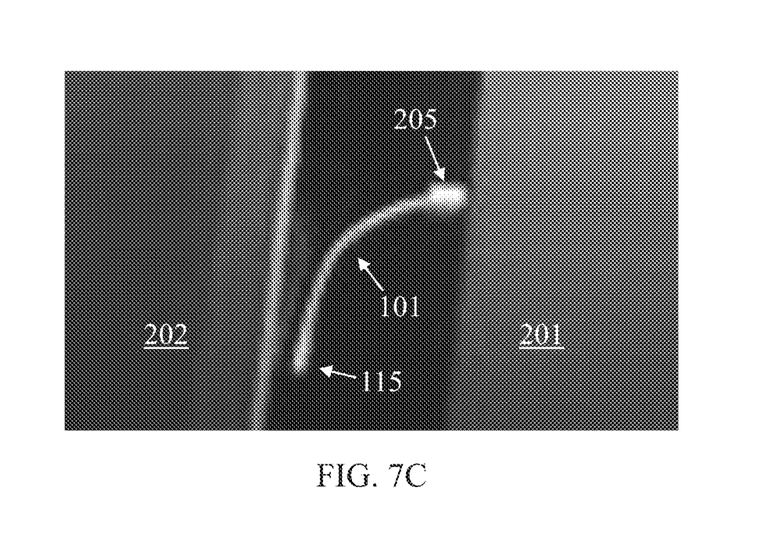

For forming hinge 120 in vascular access wire 101 shown in FIG. 5C, wire 101 can be placed in rigid channel 204 with distal tip 115 pointing towards surface 206 and niche 207, then pushed gently until distal tip 115 is in contact with niche 207 and portion of distal tip 115 is supported (e.g., nests) in niche 207 such that it is prevented from shifting transversely to pushing axis PA. As such, an unsupported length of core member 103, equal to unsupported distance 208, extends between channel portion 205 and niche 207 and is free to buckle or bend transversely to pushing axis PA, while a supported length of core member 103 proximally to the unsupported length is held in rigid channel 204 and prevented from buckling or bending transversely to pushing axis PA. FIGS. 7A-7C show sequential frames visualizing a distal portion of an exemplary vascular access wire like wire 101 in an exemplary process of forming a hinge like hinge 120, using a fixture like fixture 200. FIG. 7A shows the initial setup wherein an unsupported length 210 extends via channel portion 205 and distally supported in niche 207. Then wire 101 is pushed towards surface 206 (along pushing axis PA) firmly enough so that it creates bending and/or buckling of unsupported length 210 (FIG. 7B), and optionally afterwards additional length of wire 101 exits channel portion 205 until distal tip 115 is forced out of niche 207 (FIG. 7C). in some embodiments, unsupported length 210 includes distal tip 115 and a portion of slender segment 113, such that the bending and/or buckling occurs therealong, proximally adjacent to distal tip 115. In some embodiments, the properties of core member 103, the chosen magnitude of unsupported distance 208 and/or the force applied for pushing wire 101 resulting in the bending and/or buckling causes fixed alternation of a straight aligned length of core member 103 and/or fixed deformation (e.g., by way of plastic deformation) a portion of core member 103 into a curved length.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed disclosure.

Throughout this disclosure, a numerical value of a parameter, feature, characteristic, object, or dimension, may be stated or described in terms of a numerical range format. Such a numerical range format, as used herein, illustrates implementation of some exemplary embodiments of the disclosure, and does not inflexibly limit the scope of the exemplary embodiments of the disclosure. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the disclosure, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the disclosure which are illustratively described and presented in combination or sub-combination in the context or format of a single embodiment, may also be illustratively described and presented in the context or format of a plurality of separate embodiments.

Although the disclosure has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present disclosure. To the extent that section headings are used, they should not be construed as necessarily limiting.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A vascular access wire, comprising:
an elongated core member; and
a distal tip comprising a crank configured with a crank distal surface and a crank center of rotation;
wherein the crank is configured to rotate about the crank center of rotation when the core member is sufficiently loaded axially and when the crank distal surface is pressed against a wall of a target blood vessel, for triggering or affecting a deflecting and/or a deforming of the core member proximally to the crank.

2. The vascular access wire according to claim 1, wherein the deflecting and/or deforming includes buckling, bending and/or rotating.

3. The vascular access wire according to claim 1, wherein the crank distal surface is curved, and the crank center of rotation coincides with a center of curvature of the crank distal surface or is adjacent thereto.

4. The vascular access wire according to claim 3, wherein the crank distal surface has a crank radius of curvature within a range of 0.1 mm to 0.5 mm, optionally particularly about 0.25 mm.

5. The vascular access wire according to claim 1, wherein the core member includes, or merges with the distal tip through, a hinge configured to facilitate and/or allow articulation of the crank thereabout for converting an axial motion of the core member to a rotational motion of the crank and/or for converting a rotational motion of the crank to an axial motion of the core member.

6. The vascular access wire according to claim 5, wherein a distance of the hinge from the crank center of rotation is smaller than diameter of the blood vessel.

7. The vascular access wire according to claim 6, wherein the distance of the hinge from the crank center of rotation is equal to or smaller than about 2 mm, or optionally particularly equal to or smaller than about 1 mm.

8. The vascular access wire according to claim 5, wherein the hinge is configured as a flexing portion of the core member and includes a curved length along which the core member is fixedly deviated laterally relatively to straight aligned portions of the core member proximally and distally adjacent to the curved length.

9. The vascular access wire according to claim 8, wherein the flexing portion is about 0.5 mm or less in length.

10. The vascular access wire according to claim 1, configured such that the crank is prevented from rotating about the crank center of rotation when the core member is axially loaded with a first axial force smaller than a predetermined compression force and/or such that the crank is forced to rotate about the crank center of rotation when the core member is axially loaded with a second axial force greater than the predetermined compression force.

11. The vascular access wire according to claim 10, wherein the predetermined compression force is within a range of 0.1 N to 2 N, optionally particularly within a range of 0.2 N to 0.8 N.

12. The vascular access wire according to claim 1, further comprising:
a cylindrical coil member extending longitudinally around a length of the core member;
wherein the distal tip fixedly joining distal ends of the core member and of the coil member.

13. The vascular access wire according to claim 12, wherein the distal tip is formed by way of welding and/or fusing together portions of the core member and the coil member.

14. The vascular access wire according to claim 13, wherein the distal tip includes most or all heat-affected zone resulted from the welding and/or fusing.

15. The vascular access wire according to claim 1, wherein the distal tip includes a spherical-dome-shaped portion having a distally pointing apex.

16. The vascular access wire according to claim 1, wherein the core member includes a slender segment extending between a proximal widened segment and distal widened segment, such that the deflecting and/or the deforming is subjected to occur in the slender segment.

17. The vascular access wire according to claim 16, wherein the slender segment includes, or merges with the distal widened segment through, a hinge configured to facilitate and/or allow articulation of the crank thereabout for converting between a rotational motion of the crank and a linear motion of the core member.

18. The vascular access wire according to claim 16, wherein the distal widened segment merges with the distal tip at a distal merging portion.

19. The vascular access wire according to claim 16, wherein a volume ratio between a total volume of the distal tip and a total volume of the distal widened segment is greater than 1.3.

20. The vascular access wire according to claim 16, wherein the total volume of the distal tip is within a range of 0.2 mm^3 to 0.5 mm^3, and/or the total volume of the distal widened segment is within a range of 0.005 mm^3 to 0.03 mm^3.

21. The vascular access wire according to claim 16, wherein a length ratio between a total length of the distal tip and a total length of the distal widened segment is within a range of 1 to 2.

22. The vascular access wire according to claim 16, wherein the total length of the distal tip is about 0.35 mm or less, and/or the total length of the distal widened segment is about 0.75 mm or less.

23. The vascular access wire according to claim 16, wherein the slender segment and/or the distal widened segment is elongated and has a circular, an elliptical, or a rectangular cross section.

24. The vascular access wire according to claim 16, wherein the coiled member is configured with coil pitch greater along the slender segment than along the distal widened segment.

25. A vascular access kit, comprising:
the vascular access wire according to claim 5; and
a needle comprising a beveled opening;
wherein the hinge is positioned along the beveled opening when the distal end of the vascular access wire is in juxtaposition with a distal end of the needle.

26. A method of forming a vascular access using the vascular access kit according to claim 25, the method comprising:
   penetrating into a blood vessel with the beveled opening;
   pushing the distal tip of the vascular access wire via the beveled opening against a wall of the blood vessel until generating rotational motion of the crank about the crank center of rotation sufficient to trigger and/or affect deflecting and/or a deforming of the core member proximally to the crank, and/or sufficient to trigger or affect articulation of the crank about the hinge.

27. The method according to claim 26, further comprising:
   advancing the vascular access wire distally in the blood vessel; and
   allowing the core member to flex back and/or realign with the distal tip.

28. A method of producing the vascular access wire according to claim 12, the method comprising:
   joining a distal end of the core member and a distal end of the coil member; and
   forming the hinge.

29. The method according to claim 28, wherein the forming includes, or is caused by, fixedly altering a straight aligned length of the core member.

30. The method according to claim 28, wherein the forming includes, or is caused by, fixedly deforming a portion of the core member into a curved length.

31. The method according to claim 28, wherein the forming includes pushing the core member along a chosen pushing axis against a surface perpendicular to the pushing axis.

32. The method according to claim 31, wherein the pushing is performed while a chosen unsupported length of core member is allowed to buckle or bend transversely to the pushing axis and a supported length of core member proximally to the unsupported length is prevented from buckling or bending transversely to the pushing axis.

33. The method according to claim 31, wherein a portion of the distal tip is prevented from shifting transversely to the pushing axis and/or is supported in a niche surrounded by the surface.

34. The method according to claim 28, further comprising shaping the distal tip.

35. The method according to claim 34, wherein the forming follows the joining and/or the shaping.

36. The method according to claim 34, wherein the joining includes, or results in, the shaping.

37. The method according to claim 34, wherein the distal tip shaped into forming the crank which includes a spherical-dome-shaped portion having a distally pointing apex.

38. The method according to claim 34, wherein the shaping includes shaping a pre-shaped tip into the distal tip.

39. The method according to claim 38, wherein the joining includes welding and/or fusing together pre-fused portions of the core member and the coil member.

40. The method according to claim 39, wherein the pre-fused portions are configured to form a weld pool for facilitating the welding and/or fusing.

41. The method according to claim 39, wherein the distal tip is configured to sustain most or all heat-affected zone resulting from the welding and/or fusing, such that the core member adjacent to the hinge is structurally and/or functionally unaffected by the welding and/or fusing.

* * * * *